United States Patent [19]

Neumann et al.

[11] Patent Number: 5,801,276

[45] Date of Patent: Sep. 1, 1998

[54] PROCESS FOR THE PREPARATION OF HYDROXYPIVALIC ACID

[75] Inventors: Karl-Heinz Neumann, Sankt Augustin; Winfried Joentgen, Köln; Dieter Heitkamp, Burscheid; Helmut Fiege, Leverkusen, all of Germany

[73] Assignee: Bayer Aktiengesellschaft, Leverkusen, Germany

[21] Appl. No.: 910,442

[22] Filed: Aug. 5, 1997

[30] Foreign Application Priority Data

Aug. 16, 1996 [DE] Germany .................... 196 32 922.1

[51] Int. Cl.$^6$ .................................................. C07C 51/235
[52] U.S. Cl. .................................................. 562/531
[58] Field of Search ....................................... 562/531

[56] References Cited

U.S. PATENT DOCUMENTS 3,799,977  3/1974  Rutledge ................. 260/531

FOREIGN PATENT DOCUMENTS 4324888  10/1968  Japan .
53-077010  12/1976  Japan .

OTHER PUBLICATIONS

Monatshefte Für Chemie 95 H.P. Frank, et al., Über die Herstellung von Hydroxypivalinsäure und deren Polyester, pp. 410–414, (1964).

J.H. Payne, et al., The Oxidation of Aldehydes with Hydrogen Peroxide, vol. 63, pp. 226–228, (Jan. 1941).

H. Frank, et al., "Preparation of Hydroxypivalic Acid and Its Polyesters", Monatsh., 95, (2), 410–14, (1964), (abstract only from CA 61,12099).

H.P. Frank et al: "Über die Herstellung von Hydroxypivalinsäure und deren Polyester" Monatshefte fur Chemie., vol. 95, 1964, pp. 410–414.

J.H. Payne et al.: "The oxidation of adehydes with hydrogen peroxide" Journal of the American Chemical Society., vol. 63, 1941 DC US, pp. 226–228.

Chemical Abstracts, vol. 71, No. 7, Aug. 18, 1969, Columbus, Ohio, US; abstract No. 30073j, Huang, Ching-Yun et al.: "2,2-dimethyl-3-hydroxypropionic acid" p. 248.

*Primary Examiner*—Gary Geist
*Assistant Examiner*—Rosalynd Keys
*Attorney, Agent, or Firm*—Sprung Kramer Schaefer & Briscoe

[57] ABSTRACT

Hydroxypivalic acid can be prepared by oxidation of hydroxypivalaldehyde with hydrogen peroxide by metering the hydrogen peroxide, as the oxidizing agent, into an aqueous hydroxypivalaldehyde reservoir in the temperature range from 60° to 80° C. such that a hydrogen peroxide concentration of 4% by weight, based on the total weight of the reaction mixture, is not exceeded, and ending the addition of hydrogen peroxide as soon as the concentration of hydroxypivalaldehyde in the reaction mixture falls below 1% by weight.

4 Claims, No Drawings

PROCESS FOR THE PREPARATION OF HYDROXYPIVALIC ACID

BACKGROUND OF THE INVENTION

1. Field of the Invention

The invention relates to a process for the preparation of hydroxypivalic acid by oxidation of hydroxypivalaldehyde with hydrogen peroxide, in which the oxidizing agent is metered into an aqueous hydroxypivalaldehyde reservoir in the temperature range from 60° to 80° C. such that a concentration of hydrogen peroxide of 4% by weight in the reaction mixture is not exceeded, and the addition of hydrogen peroxide is ended as soon as the hydroxypivalaldehyde concentration in the reaction mixture falls below 1% by weight.

Hydroxypivalic acid is an important starting material for the preparation of water-based paint systems, which are increasingly gaining in importance.

2. Description of the Related Art

Hydroxypivalic acid can be prepared by potassium permanganate oxidation of neopentylglycol or by Cannizzaro reaction of hydroxypivalaldehyde. Both processes have disadvantages. Thus the yield in the oxidation of neopentylglycol is low, while the Cannizzaro reaction leads to molar amounts of neopentylglycol as a coupling product. Both processes are therefore unattractive from an industrial standpoint. As well as by these two preparation processes, hydroxypivalic acid can also be obtained by air/$O_2$ oxidation of neopentylglycol or by hydrogen peroxide oxidation of hydroxypivalaldehyde. The oxidation of neopentylglycol with $O_2$ or air over a Pd/C or Pt/C catalyst in alkaline aqueous solution to give hydroxypivalic acid is described, for example, in JP 53/77 010 (1978) and in U.S. Pat. No. 3,799,977. Data on the yield and selectivity are lacking completely in U.S. Pat. No. 3,799,977, and in JP 53/77 010 a very dubious yield of 100% is stated, this being based merely on the comparison of IR bands of the sodium hydroxypivalate prepared with a pure sample of this substance. Since, with neopentylglycol, a starting compound with two completely identical hydroxyl groups is employed, the expert knows that intermediate stages and superoxidation products, which can be separated off from the desired product only at great expense, are formed during the oxidation. In addition, at least molar amounts of NaCl or $Na_2SO_4$, which must be disposed of, are formed as a result of the neutralization of the reaction mixture. All of this does not support an industrial preparation of hydroxypivalic acid by this route.

Hydroxypivalic acid can furthermore be prepared by oxidation of hydroxypivalaldehyde with hydrogen peroxide. This process was described for the first time in Monatshefte für Chemie 95 (1964), 410, and was dealt with again in a revised variant in JP 43/24 888 (1968). In the process according to the Monatshefte, an amount of 50 mol % of a 30% strength aqueous hydrogen peroxide solution, based on the hydroxypivalaldehyde employed, is added and the reaction batch is stirred at 50° C. for 8 hours. Since a high concentration of hydrogen peroxide is used in the initial phase of this process, such a process variant presents great safety risks on an industrial scale. The low reaction temperature of 50° C. furthermore leads to a long reaction time, and therefore to a poor space/time yield. Since $H_2O_2$ dissociates only slowly at this temperature, unreacted $H_2O_2$ can also be entrained into the working-up stages and undergo concentration there. After several stages of working up via the Na salt of hydroxypivalic acid, a contaminated hydroxypivalic acid having a melting range of 100° to 122° C. is isolated in the Monatshefte, while the melting point according to literature data is 124° to 126° C. Even if the resulting crude hydroxypivalic acid is regarded as pure, the yield is only about 69% of the theoretical yield, based on the hydroxypivalaldehyde employed; the extremely wide melting point range indicates, however, that the yield of pure end product is significantly lower.

JP 43/24 888 describes a revision of the process according to the Monatshefte using a catalyst which is capable of dissociating $H_2O_2$. Very fine particles of gold, platinum, silver or glass and UV light having a wavelength of 2000 to 4000 Å are stated as suitable catalysts. In the embodiment examples, however, only the use of Ag powder is described. The oxidation of hydroxypivalaldehyde is carried out here with a molar $H_2O_2$ excess of up to 20% in the temperature range from 80° to 85° C. In contrast to the process in the Monatshefte, the amount of $H_2O_2$ is metered in within a period of 1 to 3 hours. In a further example in JP 43/24 888, the oxidation of the hydroxypivalaldehyde is carried out without a catalyst, but in two phases in benzene/water with 30% strength aqueous $H_2O_2$ solution, which is also metered in over a period of 3 hours in a 20% molar excess, in the temperature range from 58° to 60° C. This process therefore also has quite a few disadvantages. On the one hand, the Ag catalyst employed in the examples is relatively expensive. The catalyst must be separated off either by filtration or by distillation of the product, and worked up again. Reworking of the embodiment examples of JP 43/24 888 furthermore shows that when the $H_2O_2$ oxidation has ended, only 65 to 68% of the theoretical yield of hydroxypivalic acid, determined with the aid of gas chromatography analysis (GC) with an internal standard, has formed in the reaction solution. JP 43/24 888 furthermore describes working up by distillation for purification of the pivalic acid, but in a reworking only 28% of the hydroxypivalic acid originally present in the aqueous oxidation solution could be distilled off at 156° to 159° C./33 mbar. As well as making the process more expensive by using an excess of $H_2O_2$, this again presents the safety risks already mentioned above, especially if a readily flammable solvent, such as benzene, is additionally employed. A combustible waste gas composed of various amounts of $H_2$, $O_2$, CO and $CO_2$, depending on the progress of the reaction, is furthermore formed during $H_2O_2$ oxidation of hydroxypivalaldehyde to give hydroxypivalic acid; if an excess of $H_2O_2$ is metered in, this waste gas situation is intensified further. Finally, if excess $H_2O_2$ is metered in, higher concentrations of peroxide are obtained toward the end of the reaction, and these are unacceptable for safety reasons on transfer of the process to an industrial scale.

Other catalysts which have been proposed for oxidation of aliphatic aldehydes with $H_2O_2$, such as, for example, $(NH_4)_6Mo_7O_{24} \times 4H_2O$ or $CeCl_2 \times 7H_2O$ (Tetrahedron Letters 25 (1984), 173–176; Israel J. of Chem. 24 (1984), 134–143) also present problems during isolation of hydroxypivalic acid if they are applied to oxidation of hydroxypivalaldehyde. Yellow solutions are formed as a result of these catalysts, and must be decolorized expensively by addition of active charcoal before the isolation.

SUMMARY OF THE INVENTION

There therefore continued to be the need to have available a process for the $H_2O_2$ oxidation of hydroxypivalaldehyde to hydroxypivalic acid which avoids the disadvantages listed. Such a process is provided according to the invention, in which a) aqueous $H_2O_2$ is metered into the aqueous reservoir of hydroxypivalaldehyde as a function of the conversion such that a concentration of $H_2O_2$ of 4% by weight in the total reaction batch is not exceeded, b) the oxidation reaction is carried out at 60° to 80° C. and c) the addition of $H_2O_2$ is ended when the concentration of hydroxypivalaldehyde in the reservoir falls to below 1% by weight of the total amount of reaction mixture.

DETAILED DESCRIPTION OF THE INVENTION

The invention accordingly relates to a process for the preparation of hydroxypivalic acid by oxidation of hydroxypivalaldehyde with hydrogen peroxide, which comprises metering an aqueous hydrogen peroxide solution into an aqueous hydroxypivalaldehyde reservoir at 60° to 80° C. such that the concentration of hydrogen peroxide does not exceed 4% by weight of the total weight of the reaction mixture, and ending the addition of hydrogen peroxide when the concentration of hydroxypivalaldehyde falls below 1% by weight of the total weight of the reaction mixture.

It is assumed that the process according to the invention agrees with the following equation:

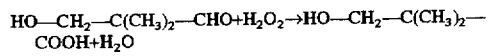

(for the mechanism, cf. for example: J. Am. Chem. Soc. 63, (1941), page 226).

The hydroxypivalaldehyde employed can be prepared by base-catalyzed condensation of isobutyraldehyde with formaldehyde, as is described in many instances. Possible bases are, for example, trialkylamines (German Offenlegungsschrift 19 57 591), $Na_2CO_3$ (JP 43/24 888) or alkali metal or alkaline earth metal hydroxides (Chem. Ber. 102, (1969), 1606). In the process according to the invention, hydroxypivalaldehyde is employed in aqueous solution, which is present at higher concentrations as a melt at slightly elevated temperature; the concentration of pivalaldehyde in this is 40 to 80% by weight, preferably 50 to 70% by weight, based on the total amount of this solution or melt.

$H_2O_2$ as the oxidizing agent is employed in aqueous solution with an $H_2O_2$ concentration of 5 to 70% by weight, preferably 20 to 50% by weight of $H_2O_2$ in the total solution. In the process according to the invention, $H_2O_2$ is metered in as a function of its consumption such that its concentration in the reaction mixture does not exceed 4% by weight, preferably 2.5% by weight, based on the total weight of the reaction mixture. The addition of $H_2O_2$ here is accompanied continuously, for example, by iodometric titration and by gas chromatography analysis (GC) with the internal standard of the hydroxypivalaldehyde still present, and is interrupted when the concentration of hydroxypivalaldehyde falls below 1% by weight, that is to say the hydroxypivalaldehyde is present in a residual amount of 0.05 to 0.99% by weight, preferably 0.2 to 0.95% by weight, based on the total weight of the reaction mixture. It has been found here that about 75 to 85 mol % of $H_2O_2$, based on the molar amount of hydroxypivalaldehyde employed, is required. There are slight variations within this range, depending on the size of the reaction vessel and evidently depending on the specific wall area per unit volume of reaction mixture. For smaller batches, $H_2O_2$ consumptions in the upper part of the range stated (about 80 to 85 mol % of $H_2O_2$) are thus consumed, while in industrial reactors, consumptions of below this down to 75 mol % of $H_2O_2$ have been observed. The yield of hydroxypivalic acid, based on the hydroxypivalaldehyde employed, is about 72 to 76% of the theory in solution. It has furthermore been observed that an amount of $H_2O_2$ greater than that stated above leads to an impaired selectivity for hydroxypivalic acid; this is accompanied by an increased $CO_2$ emission, which suggests a more extensive oxidative degradation of the hydroxypivalic acid.

The process according to the invention is carried out in the range from 60° to 80° C., preferably in the range from 63° to 78° C.

The process according to the invention has economic advantages in respect of its handling, its safety aspects and its selectivities. Thus, a catalyst-free oxidation process has the advantage that at least one working-up step for removal of the catalyst (filtration, centrifugation) and for removal of any coloring soluble catalysts present (active charcoal treatment) is omitted. The advantageous temperature program in the range from 60° to 80° C. has furthermore been found, while in the process according to the Monatshefte, a temperature of 50° C. is maintained, evidently for safety reasons; as a result, the metering time for $H_2O_2$ can be reduced to about 3 to 4 hours, while in the process according to the Monatshefte, a reaction time of 8 hours is required, which results in a very low space/time yield. It has furthermore been found that when temperatures above 80° C. are used, regardless of the use of a catalyst, a noticeable dissociation of $H_2O_2$ occurs; as in JP 43/24 888, this can be compensated only by employing a significantly higher amount of $H_2O_2$, but this means that the entire process becomes unnecessarily more expensive. The process according to the invention is thus astonishingly advantageous both in respect of the amount of $H_2O_2$ required and in respect of the selectivity for hydroxypivalic acid which can be achieved.

EXAMPLE 1
(Hydroxypivalaldehyde HPA)

1745.8 g of 35% strength formalin solution (20.35 mol) and 101.0 g of triethylamine (1.0 mol) were initially introduced into a 4 l four-necked flask with a stirrer, internal thermometer, intensive cooler and dropping funnel, and were heated to 55° C. under an $N_2$ atmosphere. When this temperature was reached, 1456.8 g of 99% pure isobutyraldehyde (20.0 mol) were added dropwise in the course of 45 minutes. The reaction was exothermic; in order to maintain the temperature of 55° C., it was necessary to cool thoroughly. When the addition of isobutyraldehyde had ended, the reaction mixture was heated up from 55° C. to 90° C. in the course of 1 hour. It was then allowed to cool again and the intensive cooler was replaced by a distillation device with a 500 ml receiver flask. To remove unreacted isobutyraldehyde, a total of 388.7 g of distillate were stripped off at a bottom temperature of 55° to 57° C./175 to 185 mbar. 2820 g of aqueous HPA solution with a content of 64.78% (GC internal standard) ≙17.9 mol ≙89.5% of the theoretical yield were obtained as the residue.

EXAMPLE 2
(Oxidation of HPA with $H_2O_2$ to give hydroxypivalic acid)

During the oxidation, the HPA conversion, by means of GC analyses, and the $H_2O_2$ concentration, by iodometric titration, were determined concomitantly. 574 g of a molten, aqueous solution containing 3.39 mol of HPA were initially introduced into a 2 l four-necked flask with a stirrer, reflux condenser, dropping funnel, internal thermometer, pH electrode and redox electrode and were heated to 70° C. At this temperature, 222 ml of 35% strength aqueous $H_2O_2$ solution (2.58 mol) were metered in over a period of 3 hours such that a peroxide concentration of 2.5% by weight was not exceeded. When the metering had ended, the residual HPA concentration was determined by a GC analysis. In the present example, a further 14.5 ml of 35% strength $H_2O_2$ solution were metered in over a period of 20 minutes with the aim of forcing the HPA concentration below 1% by weight. The total amount of $H_2O_2$ was thus 236.5 ml ≙267.2 g ≙93.54 g of $H_2O_2$ ≙2.75 mol. During the metering of $H_2O_2$, about 21 l of a combustible waste gas were formed, this being composed of varying amounts of $H_2$, $O_2$, CO, $CO_2$ and volatile organic compounds, depending on the conversion. When the metering of $H_2O_2$ had ended, the mixture was subsequently stirred at 70° C. for a further hour and was allowed to cool, and the HPA content of the solution was tested by means of GC with an internal standard. Yield: 795.6 g of aqueous solution, HPA content: 37.22% (GC) ≙296.1 g of hydroxypivalic acid=2.507 mol ≙74.0% of the theoretical yield, based on the HPA employed.

EXAMPLE 3
(for comparison)

726.2 g of an aqueous solution which comprised 3.035 mol of crude HPA were initially introduced into the apparatus described in Example 2 and were heated to 60° C. 349.9 g (3.59 mol) of a 35% strength aqueous $H_2O_2$ solution were added dropwise into the reservoir, which had a temperature of 60° to 70° C., in the course of 90 minutes. Thereafter, the mixture was subsequently stirred at the same temperature for a further 30 minutes and the excess $H_2O_2$ was then destroyed by boiling in the course of 4 hours. For final removal of residual peroxides, 18.5 ml of 39% strength sodium hydrogen sulfite solution were also added. The reaction solution was then brought to pH=2.5 with 96% strength $H_2SO_4$. A total of 1.66 mol of hydroxypivalic acid ≙54.7% of the theoretical yield was detected by means of GC analysis (internal standard). It was found as a result that the use of an excess of $H_2O_2$ (HPA:$H_2O_2$~1:1.2 mol) and rapid metering leads to higher $H_2O_2$ concentrations in the batch, and brings no advantage; indeed, the hydroxypivalic acid is in fact degraded by superoxidation.

EXAMPLE 4
(for comparison)

555 g of a molten aqueous solution containing 3.51 mol of HPA, which had been prepared analogously to Example 1, were initially introduced into the apparatus described in Example 2. 350 mg of silver powder were added to the reservoir and the mixture was heated to 80° C. At this temperature, 400 g of 32% strength aqueous $H_2O_2$ solution ≙4.25 mol of $H_2O_2$ were added dropwise in the course of 150 minutes (including interruptions for peroxide titrations). When the addition had ended, the mixture was stirred at 80° C. for a further 30 minutes. It was then allowed to cool, the silver catalyst was filtered off and the catalyst was rinsed with water. 917.6 g of an aqueous solution with a hydroxypivalic acid content of 29.85% (GC internal standard)= 273.9 g=2.32 mol ≙66.1% of the theoretical yield were obtained.

What is claimed is:

1. A process for the preparation of hydroxypivalic acid by oxidation of hydroxypivalaldehyde with hydrogen peroxide, which comprises metering an aqueous hydrogen peroxide solution into an aqueous reservoir of hydroxypivalaldehyde at 60° to 80° C. such that the concentration of hydrogen peroxide does not exceed 4% by weight of the total weight of the reaction mixture, and ending the addition of hydrogen peroxide when the concentration of hydroxypivalaldehyde falls below 1% by weight of the total weight of the reaction mixture.

2. The process of claim 1, wherein the hydroxypivalaldehyde is employed as an aqueous solution or melt having a content of 40 to 80% by weight, based on the solution or melt.

3. The process of claim 2, wherein the content of hydroxypivalaldehyde is 50 to 70% by weight, based on the solution or melt.

4. The process of claim 1, wherein the concentration of hydrogen peroxide does not exceed 2.5% by weight of the total weight of the reaction mixture.

* * * * *